US00PP11618P

United States Patent [19]

Trees

[11] Patent Number: Plant 11,618

[45] Date of Patent: Nov. 7, 2000

[54] GUINEA IMPATIENS PLANT NAMED 'BALCEBWIUM'

[75] Inventor: Scott C. Trees, Nipomo, Calif.

[73] Assignee: Ball Floraplant, a division of Ball Horticultural Co., West Chicago, Ill.

[21] Appl. No.: 09/255,940

[22] Filed: Feb. 20, 1999

[51] Int. Cl.[7] ..... A01H 5/00

[52] U.S. Cl. ..... Plt./318

[58] Field of Search ..... Plt./318

*Primary Examiner*—Bruce R. Campell

*Assistant Examiner*—Kent L. Bell

*Attorney, Agent, or Firm*—C. A. Whealy

[57] ABSTRACT

A new and distinct cultivar of New Guinea Impatiens plant named 'Balcebwium', characterized by its numerous purple red-colored flowers; floriferousness; upright and mounded plant habit; medium plant size; good basal branching; and dark green leaves.

1 Drawing Sheet

BACKGROUND OF THE INVENTION

The present invention relates to a new and distinct cultivar of New Guinea Impatiens plant, botanically known as *Impatiens hawkeri,* and hereinafter referred to by the cultivar name 'Balcebwium'.

The new Impatiens is a product of a planned breeding program conducted by the Inventor in Arroyo Grande, Calif. The objective of the breeding program was to develop new cultivars with excellent basal branching, compact upright growth habit, numerous large flowers, and interesting flower and foliage colors.

The new Impatiens originated from a cross made by the Inventor of the *Impatiens hawkeri* cultivar 'BFP-523 Deep Red', disclosed in U.S. Plant Pat. No. 9,521, as the male, or pollen parent, with the *Impatiens hawkeri* cultivar 'Prepona', disclosed in U.S. Plant Pat. No. 9,150, as the female, or seed parent. The cultivar 'Balcebwium' was discovered and selected by the Inventor as a flowering plant within the progeny of the stated cross in a controlled environment in Arroyo Grande, Calif., in December, 1996. Plants of the new Impatiens differ from plants of both parent cultivars primarily in flower color as plants of both parent cultivars have dark red colored flowers.

Asexual reproduction of the new cultivar by terminal cuttings taken at Arroyo Grande, Calif., has shown that the unique features of this new Impatiens are stable and reproduced true to type in successive generations of asexual reproduction.

SUMMARY OF THE INVENTION

The following traits have been repeatedly observed and are determined to be the unique characteristics of 'Balcebwium'. These characteristics in combination distinguish 'Balcebwium' as a new and distinct cultivar:

1. Numerous purple red-colored flowers; very freely flowering.
2. Upright and mounded plant habit.
3. Medium plant size.
4. Good basal branching.
5. Dark green leaves.

The new Impatiens can be compared to the *Impatiens hawkeri* cultivar 'Papete', disclosed in U.S. Plant Pat. No. 8,457. However, in side-by-side comparisons conducted in Arroyo Grande, Calif., plants of the new Impatiens differ from plants of the cultivar 'Papete' in the following characteristics:

1. Plants of the new Impatiens are not as freely branching as plants of the cultivar 'Papete'.
2. Plants of the new Impatiens are more freely flowering than plants of the cultivar 'Papete'.
3. Flower color of plants of the new Impatiens is more red than flower color of plants of the cultivar 'Papete'.

A detailed comparison of plants of the cultivar 'Balcebwium' and the cultivar 'Papete' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of 'Balcebwium'. Flower and foliage colors in the photograph may appear different than the actual colors due to light reflectance.

DETAILED BOTANICAL DESCRIPTION

The cultivar 'Balcebwium' has not been observed under all possible environmental conditions. The phenotype may vary somewhat with variations in environment such as temperature and light intensity, without, however, any variance in genotype. The following observations, measurements and comparisons describe plants grown in 10-cm pot in Arroyo Grande, Calif., under commercial practice in a glass-covered greenhouse with day temperatures about 20 to 22° C., night temperatures about 18 to 20° C., and light levels generally about 2,500 to 3,000 footcandles.

In the following description, color references are made to The Royal Horticultural Society Colour Chart except where general terms of ordinary dictionary significance are used.

Botanical classification: *Impatiens hawkeri* cultivar 'Balcebwium'.

Parentage:

*Male parent.*—*Impatiens hawkeri* cultivar 'BFP-523 Deep Red', disclosed in U.S. Plant Pat. No. 9,521.

*Female parent.*—*Impatiens hawkeri* cultivar 'Pepona', disclosed in U.S. Plant Pat. No. 9,150.

Propagation:

*Type cutting.*—Terminal cuttings.

*Time to initiate roots.*—About 7 days at 18° C.

*Time to develop roots.*—About 21 days at 18° C.

*Rooting habit.*—Fibrous, fine, freely branching.

Plant description:

*General appearance.*—Upright and mounded; medium plant size. Appropriate for 10 and 12.5-cm containers.

*Growth and branching habit.*—Good basal branching with about seven or eight lateral branches at the base, dense and bushy growth. Pinching, that is, removal of the terminal apices, is usually not required.

*Crop time.*—Starting with a rooted cutting, about ten weeks are required to produced a finished flowering plant in a 10-cm container.

*Plant height.*—About 16 to 20 cm.

*Plant width.*—About 20 to 25 cm.

*Lateral banches.*—Length: About 11 to 15 cm. Diameter: About 6 to 8 mm. Internode length: About 4 to 5 cm. Color: 146D with maroon, 183C, streaks.

*Foliage description.*—Leaves simple, generally symmetrical, abundant, in whorls or opposite. Length: About 6 to 8 cm. Width: About 2 to 3 cm. Shape: Lanceolate. Apex: Acuminate. Base: Attenuate. Margin: Serrate/ciliate. Texture: Slightly rugose; glossy; slightly pubescent along lower surface's veins. Color: Young foliage, upper surface: 137A. Young foliage, lower surface: 137C. Fully expanded foliage, upper surface: 137A. Fully expanded foliage, lower surface: 147B. Venation, upper surface: 185C. Venation, lower surface: 183C. Petiole: Length: About 1 to 2 cm. Diamete: About 2 to 3 mm. Color: 185A.

Flower description:

*Flower type and habit.*—Purple red-colored flowers. Very freely and continuously flowering. Flowers arise from leaf axils. Usually about eight to fifteen flowers and flower buds per lateral branch. Flowers positioned mostly above the foliage and typically face outward to upward. Flowers generally flat and rounded. Flowers persistent.

*Flowering season.*—Year-round under greenhouse conditions. In the garden, flowering is continuous from spring until fall.

*Flower longevity.*—Flowers last about one week depending on temperature, light level, and water status.

*Flower size.*—Diameter: About 6.4 to 6.7 cm.

Depth: About 1 to 1.5 cm.

*Flower buds.*—Length: About 2.1 to 2.3 cm. Diameter: About 1.2 to 1.4 cm. Shape: Elliptic. Color: Close to 53B.

*Petals.*—Quantity: Five, overlapping. Length: About 2 to 2.5 cm. Width: About 3.1 to 4.6 cm. Shape: Cordate. Apex: Retuse. Base: Attenuate. Margin: Entire. Texture: Velvety. Color: When opening, upper surface: 53A. When opening, lower surface: 53B. Fully opened, upper surface: 53B. Fully opened, lower surface: 53C.

*Spur.*—Length: About 6 cm. Shape: Narrow and curved. Color: 183B.

*Peduncles.*—Length: About 5 to 6 cm. Angle: About 45° to the lateral branch. Strength: Strong. Color: 183C.

*Reproductive organs.*—Androecium: Stamen number: Five, anthers fused, filaments free. Anther shape: Obovate. Anther color: 53C. Pollen amount: Moderate. Pollen color: 10D. Gynoecium: Five-loculate fused. Ovary color: 141B.

Disease resistance: Resistance to pathogens common to Impatiens has not been observed.

Seed development: Seed production has not been observed.

CHART A

| CHARACTERISTIC | 'BALCEBWIUM' | 'PAPETE' |
|---|---|---|
| PLANT HEIGHT | About 16 to 20 cm | About 17 to 19 cm |
| PLANT WIDTH | About 20 to 25 cm | About 20 to 25 cm |
| NUMBER OF LATERAL BRANCHES | About 7 to 8 | About 9 to 12 |
| STEM COLOR | 146D; streaks, 183C | 187B |
| LEAF SHAPE | Lanceolate | Ovate |
| LEAF COLOR, UPPER SURFACE | 137A | 139A |
| PETIOLE LENGTH | About 1 to 2 cm | About 2 to 3 cm |
| QUANTITY OF FLOWERS AND BUDS PER LATERAL STEM | About 8 to 15 | About 4 to 9 |
| FLOWER DIAMETER | About 6.4 to 6.7 cm | About 5.8 to 6.5 cm |
| SPUR LENGTH | About 6 cm | About 7 cm |
| SPUR COLOR | 183B | 187B |
| PETAL COLOR, FULLY OPENED, UPPER SURFACE | 53B | Between 74A and 78A |
| PETAL COLOR, FULLY OPENED, LOWER SURFACE | 53C | 78B |
| PEDUNCLE COLOR | 183C | 187B |

It is claimed:

1. A new and distinct cultivar of New Guinea Impatiens plant named 'Balcebwium', as illustrated and described.

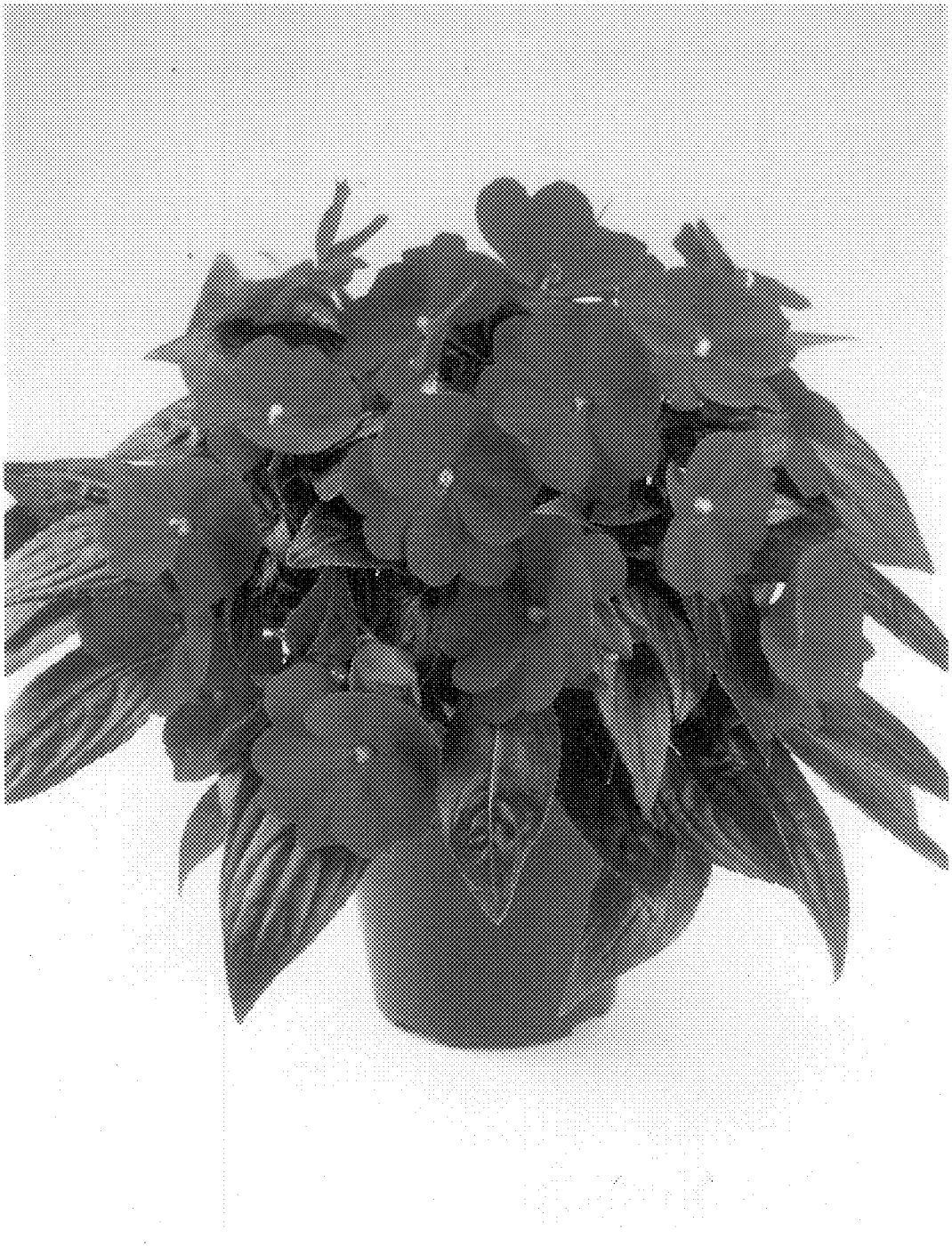

* * * * *